United States Patent [19]

Smid et al.

[11] Patent Number: 5,024,232
[45] Date of Patent: Jun. 18, 1991

[54] NOVEL RADIOPAQUE HEAVY METAL POLYMER COMPLEXES, COMPOSITIONS OF MATTER AND ARTICLES PREPARED THEREFROM

[75] Inventors: Johannes Smid, Lafayette; Israel Cabasso; Alan Obligin, both of Syracuse, all of N.Y.; H. Ralph Rawls, Boston, Mass.

[73] Assignee: The Research Foundation of State University of NY, Albany, N.Y.

[21] Appl. No.: 385,237

[22] Filed: Jul. 25, 1989

Related U.S. Application Data

[60] Division of Ser. No. 273,662, Nov. 18, 1988, Pat. No. 4,882,392, which is a continuation of Ser. No. 916,182, Oct. 7, 1986, abandoned.

[51] Int. Cl.$^5$ .................................................. A61B 6/00
[52] U.S. Cl. ..................................... 128/654; 523/117; 525/328.6; 525/330.2; 525/330.6; 525/420; 525/444; 525/445.5; 525/448; 536/76; 536/82; 604/280; 623/1; 623/2
[58] Field of Search ..................... 523/117; 525/330.2, 525/328.6, 330.6, 420, 444, 444.5, 448; 536/76, 82; 128/654; 604/280; 623/1, 2

[56] References Cited

FOREIGN PATENT DOCUMENTS 57200 4/1980 Japan .
35098 4/1981 Japan .

OTHER PUBLICATIONS

O.S., O.M. & O.P., pp. 318–324, vol. 22, No. 3 (Sep. 1966).
Journal of Dental Research-Supplement, vol. 50, 1192 (1971).
Inorganic Chemistry, vol. 10, No. 9, pp. 1896–1899 (1971).
The Dental Practitioner, pp. 51∝54 (1971).
Journal of Dentistry, vol. 1, pp. 93–97 (1972).
Journal of Dentistry, 10, No. 3, pp. 254–264 (1982).
Journal of Prosthetic Dentistry, vol. 25, No. 3, pp. 251–257 (Mar. 1971).
Journal of American Dental Association (JADA), vol. 102, pp. 347–349 (Mar. 1981).
J. Biomed. Mater. Research, vol. 5, pp. 335–357 (1971).

*Primary Examiner*—Bernard Lipman
*Attorney, Agent, or Firm*—Howard M. Ellis; Michael L. Dunn

[57] ABSTRACT

Novel radiopaqaue materials comprise heavy metal salts, such as bismuth and uraniuim salts complexed with a polymer. The metallic complexes which are permanent, nonleachable and have radiopacities at least equivalent to that of aluminum do not adversely affect the mechanical and physical properties of compositions. They are useful as medical and dental resins, in fabricating medical and dental appliances, prosthetic devices, radiation shielding devices and radiopaque polyester fabrics for clothing.

22 Claims, No Drawings

NOVEL RADIOPAQUE HEAVY METAL POLYMER COMPLEXES, COMPOSITIONS OF MATTER AND ARTICLES PREPARED THEREFROM

This invention was made with government support under grant/contracts 5R01-DE 06179-01A1 from the National Institute of Health and DMR 8504999 from the National Science Foundation. The government has certain rights in this invention.

This is a divisional of application Ser. No. 07/273,662, filed Nov. 18, 1988, now U.S. Pat. No. 4,882,392, which is a continuation of application Ser. No. 06/916,182, filed Oct. 7, 1986, now abandoned.

BACKGROUND OF THE INVENTION

The present invention relates to new and useful polymers, and more specifically, to improved nonleachable, optically transparent, homogeneous radiopaque heavy metal-containing polymer complexes, compositions of matter and articles prepared therefrom.

Translucent polymeric materials, and particularly, acrylic type resins have been widely used for years in both medical and dental applications. In dentistry, for instance, plastics are used in a broad range of materials and appliances, including removable dentures, temporary crown and bridge materials, restorative materials, impression materials, and the like. They also find many applications in medicine, such as surgical and body implants and other prosthetic devices, e.g. heart valves, blood vessels, etc. Translucent plastics are also widely used in medical appliances, such as catheters.

The desirability of imparting radiopacity to plastics used in dentistry and medicine has been recognized. In dentistry, for example, it has been difficult to detect secondary caries or underlying decalcified dentin resulting from the placement of unreinforced direct restorative resins because these materials are relatively radiolucent, and are not opaque to x-rays. Surveys have also shown that dental instruments, materials and non-fixed appliances have fractured and become embedded in soft tissues, ingested or inhaled inadvertently by patients. Although incidences of ingestion or inhalation of dental plastics are relatively rare compared with other foreign objects, the occurrence may result in a severe medical emergency or even death. The potential severity of such an incident makes it imperative to diagnose and remove such foreign bodies rapidly.

In medicine, hip joint replacements require cementing. Therefore, it would be desirable to monitor the positioning of bone cement without surgical procedure. Similarly, the ability to monitor by x-ray replacement heart valves, arteries, including the path of catheters traversing blood vessels and organ systems would be desirable. Hence, there is a need for polymeric materials with increased radiation absorption potentials which also possess the requisite nonleachable properties for safe and acceptable use in dentistry and medicine.

Heavy metal salts, like those of bismuth, barium, etc., have been used as contrast medium in diagnostic radiography. They have properties which would suggest their suitability for increasing the radiation absorption potential of medical and dental resins. As a result, substantial effort has been made to incorporate barium sulfate and other radiopaque salts, like bismuth bromide, bismuth chloride, bismuth subnitrate, etc., into polymers to render them opaque to x-rays. However, earlier radiopaque polymers containing heavy metal salts have not been totally satisfactory. Heavy metal-containing radiopaque materials fall into two principal groups: radiopaque glass containing embedded heavy metals, and polymers mixed with heavy metal salts. In the case of heavy metals embedded into radiopaque glasses, the metal is not molecularly bound to the polymer matrix, and therefore, has a tendency to weaken the composite. Moreover, because glass filler based resins lack homogeneity a further weakening of regions in the matrix results. Those regions of a composite having little or no glass are radiolucent. In addition, a light scattering effect is produced by radiopaque glasses which alters optical properties and renders them optically opaque.

Heretofore, polymers with added inorganic heavy metal salts were essentially physical mixtures, present as fine powders locked in a matrix. Their preparation resulted in an uneven distribution of the salt, and had an adverse affect on the mechanical properties of the plastic material. The salt gradually leached out of the matrix causing discoloration of the polymer and release of heavy metal toxins. The salt and polymer remained as separate distinct phases producing an opaque, cloudy material which scattered light. Mixing does not impart homogeneity between the salt and polymer.

Examples of bismuth salt-containing polymers are disclosed by E. C. Combe in the *Dental Practitioner*, 51-54 (1971); *Journal of Dental Research Supplement*, Vol. 50, 1192 (1971) and *Journal of Dentistry*, Vol. 1, 93-97 (1972). They are also described by Elzay et al in the *Journal of Prosthetic Dentistry*, Vol. 25, 251-257 (March 1971). Combe reported in the Dental Practitioner supra tests with a radiopaque self-curing crown and bridge resin then available from Coe Laboratories under the Raypaque trademark. This composition apparently comprised a heterogeneous mixture of bismuth tribromide and a polymer. Combe concluded that although Raypaque resin had greater radiopacity than other materials, the bismuth tribromide polymer mixture had lower impact strength than conventional radiolucent acrylics. Combe also reported in the Journal of Dental Research supra in 1971, that studies of 12 percent bismuth trichloride added to acrylic dough provided radiopaque polymers with transverse strength which closely approached that of the unmodified acrylic.

The 1972 Journal of Dentistry paper supra reported studies in which 8.1; 15.3; 21.7 and 26.5 percent (w/w) bismuth trichloride was dissolved in methyl methacrylate monomer before preparation of the dough. However, of the amounts listed only 8.1 percent bismuth trichloride fully dissolved in the monomer. That is, radiopaque polymers comprising bismuth trichloride in amounts of 15 percent and more did not fully dissolve in the methyl methacrylate monomer, and consequently, such nonhomogeneous polymers had significant amounts of uncomplexed, leachable heavy metal salts. In addition, the composition comprising only 8.1 percent bismuth trichloride had an inadequate amount of heavy metal to impart sufficient radiopacity properties to the polymer so it was at least equivalent to that of aluminum. The composition originally containing 8.1 percent bismuth trichloride was diluted even further when it was swelled in additional methyl methacrylate monomer in making the dental dough, resulting in a further reduction in radiopacity properties. Combe ultimately concluded that in terms of affects on mechanical properties there was little to choose. The bismuth halide polymers were also rejected because of high water absorption of the acrylics containing these additives.

Elzay et al reported on a series of heavy metal-containing heterogeneous radiopaque polymeric materials, including two prepared with bismuth subnitrate for dental prosthetic devices. The bismuth subnitrate and barium sulfate containing polymers were found unacceptable by Elzay et al as radiopaque additives for acrylic resins because of a staining effect in 26 percent of the dentures tested.

Additional radiopaque contrast media have been formed by the use of (a) other heavy metal salts, such as silver and lead; (b) heavy metals embedded in silica filler and then added to the resin composition, and (c) the use of highly halogenated polymers. Halogenated polymers or halogenated organic additives, e.g. brominated polymers have good physical properties, but the halogen functional groups tend to hydrolyze or decompose and form leachable compounds. This is especially pronounced in acidic aqueous fluids as commonly found in humans. In addition to the potential toxic effects, leaching of bromide and other halogens causes discoloration of the resin which gradually converts the polymer to a radiolucent material. The halogenated organic additives can also act to decompose the polymer. Accordingly, there is a need for improved radiopaque materials where a radiopacifying salt is molecularly bound to the polymer to form clear, homogeneous, nonleachable materials with mechanical properties which are substantially equivalent to those polymers which are free of such salts.

BRIEF SUMMARY OF THE INVENTION

The present invention relates to novel radiopaque complexes comprising heavy metal radiopacifying salts homogeneously distributed throughout the molecular level of a polymer. The radiopaque materials are comprised of heavy metal Lewis acid radiopacifying salts complexed with a polymer. The polymer comprises at least one Lewis base monomer, such as a vinyl alkyl ketone, alkyl and aryl esters of unsaturated carboxylic acids, vinyl esters of carboxylic acids, cellulose esters of carboxylic acids, linear and crosslinked polyesters, and the like. A large number of homogeneous radiopaque complexes can be prepared which include heavy metal Lewis acid salts like bismuth tribromide and uranyl nitrate complexed with polymers, such as poly (methyl methacrylate), poly (ethyl acrylate), poly (vinyl acetate), cellulose triacetate, glyptal and the like.

The radiopacifying salt is present in the polymer in an amount sufficient to impart a radiopacity which is at least equivalent to that of aluminum and which will also fully dissolve in the monomer. The homogeneous radiopaque complexes are permanent, substantially non-leachable, transparent materials; do not adversely affect the mechanical and physical properties of the compositions in which they are used, and can be employed in a broad range of medical/dental, industrial applications and products, such as in diagnostics of biomaterials, e.g. implants, dentures, restorative resins, prosthetic devices, adhesives, sutures, medical appliances, including catheters; optically transparent plastics for windows and other protective shielding devices; textiles for radiation resistant clothing for workers in occupations where they are exposed to x-rays, high energy ultraviolet radiation, and the like.

PREFERRED EMBODIMENTS OF THE INVENTION

The radiopaque materials of the present invention comprise a heavy metal Lewis acid radiopacifying salt complexed with a polymer comprising a Lewis base monomer or mixture of such monomers. That is, instead of a physical mixture of radiopaque salt and polymer resulting in uneven distributions of salt which adversely affect mechanical and physical properties, according to the present invention any heavy metal coordinate-covalently bonded salt capable of overlapping with an electron pair can be complexed with an electron pair donating monomer. Thus, an electron donating monomer, such as an ester or ketone, will readily interact with radiopaque heavy metal Lewis acid salts like bismuth tribromide, mercury bromide, etc., to form solubilized homogeneous salt-monomer complexes. The electron rich carbonyl functionality of such monomers has substantial affinity for these mild Lewis acids. This overlap of electrons from the carbonyl group to bismuth and other heavy metal ions is the basis for the interaction of these compounds and their natural compatability. The salt-monomer complexes can then be polymerized into radiopaque resins. The salt which is complexed at the molecular level is homogeneously distributed in sufficiently high concentrations to impart good radiopaque properties to the polymer without materially altering its mechanical and physical properties.

The complexing polymer may comprise at least one monomer which is capable of donating a pair of electrons, i.e. acting as a Lewis base. One group of monomers are the alkyl and vinyl alkyl ketones, such as vinyl methyl ketone, vinyl ethyl ketone, vinyl propyl ketone, methyl isopentyl ketone, ethyl isopentyl ketone, and the like. Especially included are the alkyl and aryl esters of unsaturated carboxylic acids, like acrylic, methacrylic and ethacrylic acids. Specific preferred examples include the methyl, ethyl, benzyl and butyl esters of acrylic acid and the methyl, ethyl, n-propyl, n-butyl, n-hexyl, 2-ethyl butyl, n-octyl and n-lauryl esters of methacrylic acid. Also included within this group are the methyl, ethyl, butyl, lauryl, stearyl esters of ethacrylic acid.

Other suitable Lewis base monomers which may be used to form the polymer complex include esters of unsaturated dicarboxylic acids, such as maleic acid, fumaric acid and itaconic acid. Specific representative examples include the di-n-amyl, diphenyl, dimethyl, diethyl and dibutyl esters of maleic acid; the di-n-amyl, diisoamyl and the di-n-butyl esters of fumaric acid and the dimethyl and di-n-butyl esters of itaconic acid.

The Lewis base monomers may also be selected from saturated monocarboxylic acid esters, including aliphatic and aromatic types. Specific representative examples include vinyl acetate, vinyl propionate, vinyl-2-ethyl hexanoate, vinyl laurate, vinyl benzoate, vinyl caproate and the like. Also included are the modified natural polymers, such as cellulose acetate, cellulose triacetate, cellulose acetate butyrate and cellulose stearate.

It is to be understood that the foregoing polymer complexes may also be prepared with a mixture of monomers, e.g. methyl methacrylate, ethyl acrylate, vinyl acetate, hydroxyethyl methacrylate, and the like.

The novel homogeneous radiopaque polymers may also be complexed with polyesters, especially for making fabrics for clothing to be worn by workers exposed to potentially harmful levels of radiation, such as radiologists and x-ray technicians. The polyesters especially preferred are those having ester functionality in the backbone of the polymer. They include linear and crosslinked types formed from dicarboxylic acids and a diol or triol. More specifically, the compounds intended are those of the formula:

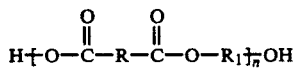

wherein R is aryl or $(CH_2)_y$ wherein y is an integer of 1 to 10, $R_1$ is aryl, substituted aryl or $(CH_2)_x$ wherein x is an integer of 1 to 6 and n is an integer of 2 to 5000. Specific representative examples of polyesters include ethylene terephthalate, poly(isophthalic acid-co-maleic anhydride), poly(lauric acid-co-glycerol), and poly(phthalic anhydride-co-glycerol) (glyptal).

Compounds which may be used to complex with the foregoing monomers include heavy metal Lewis acid radiopacifying salts which by definition includes any heavy metal electron deficient salt which will accept electron density from a Lewis base monomer and whose cation has an atomic number of at least 57. This will include heavy metals having atomic numbers of 57 to 92, and more preferably, atomic numbers of 78 to 92. Lanthanide series metals having atomic numbers of 57 to 71 although satisfactory are less preferred than the higher molecular weight metals like mercury, lead and bismuth. Rare transition metals with atomic numbers of 72 to 77 are also acceptable, but are less preferred because of lower atomic weights, high cost and their ability to form multinuclear complexes. Most preferred heavy metals include bismuth, lead, mercury and uranium. Heavy metal salts include the halides, preferably bromides. Other halides may also be employed, but are not preferred because of generally lower solubilities in most Lewis base monomers. The most preferred bismuth, mercury and uranium salts are bismuth tribromide, bismuth nitrate and acetate; uranyl bromide, nitrate and acetate; mercury nitrate and acetate, and the like.

The heavy metal Lewis acid salt should be present in an amount sufficient to impart a radiopacity to the polymer equivalent to that of aluminum while also fully dissolving in the monomer. To form heavy metal-polymer complexes having a radiopacity level equivalent to aluminum and also having a fully complexed homogeneous system, the minimum amount of heavy metal salt in the polymer will range from about 10 to about 19 percent by weight based on total polymer. Hence, in a monomer like methyl methacrylate more than 40 percent by weight bismuth tribromide can be dissolved. Polymerization of the complex yields a homogeneous transparent material which is nonleachable when in contact with an aqueous solution. Accordingly, a 1 mm pellet of poly(methyl methacrylate) containing 12.5 percent by weight bismuth tribromide has a radiopacity equivalent to 1 mm of aluminum. By contrast, those complexes prepared with heavy metal salts having relatively low solubility in the monomer, or those prepared with excess salt to polymer are cloudy or whitish indicating the presence of uncomplexed salt. Such mixtures are heterogeneous and have inferior mechanical properties.

As previously disclosed, the heavy metals of the present invention are homogeneously distributed and complexed with the polymer at the molecular level to form optically lucent radiopaque materials. Therefore, the complexed heavy metal is virtually nonleachable from the resin. Optionally however, the present invention also contemplates the addition of small amounts of crosslinking agents ranging from 1 to about 15 percent by weight. This will provide even greater resistance to leaching of the heavy metal salt from the polymer. Suitable representative examples include tetraethylene glycol dimethacrylate (TEG), ethylene glycol dimethacrylate, bisphenol-A-glycidyl methacrylate (BisGMA), and the like.

The linear radiopaque polymeric materials have molecular weights generally ranging from 10,000 to about 1,000,000, and more specifically, from about 25,000 to about 500,000.

Generally, the homogeneous radiopaque polymers of the present invention are prepared by two methods. The first involves dissolving the heavy metal salt in the monomer(s) and polymerizing in the presence of an initiator like benzoyl peroxide, azobisisobutyronitrile (ABIN), etc. More specifically, in the preparation of radiopaque polymers having carbon to carbon unsaturation, such as a vinyl group, the heavy metal salt is dissolved in the monomer, e.g. methyl methacrylate, with initiator and bulk polymerized at elevated temperatures of about 65° C. in the absence of oxygen.

The foregoing high temperature bulk method is especially adaptable for industrial uses. In polymerizations for molds or in vitro applications the heavy metal salt, e.g. uranyl nitrate 40 percent by weight, can be dissolved in the monomer, e.g. methyl methacrylate, and polymerized with ABIN at 65° C. in the absence of oxygen. The polymer is ground to form a solid polymer powder phase. A peroxide initiator, such as 0.5 percent by weight benzoyl peroxide is added to the powder. Separately, a liquid monomer phase is prepared where monomer, e.g. methyl acrylate, and a crosslinking agent, such as tetraethylene glycol dimethacrylate (TEG) are combined. The solid and liquid phases are then combined. The linear polymer powder complex will swell and coalesce in the liquid phase on thorough mixing. The dough-like material is placed in a mold, degassed and polymerized at 65° C.

Room temperature polymerizations using benzoyl peroxide as initiator and dimethyl-p-toluidine as accelerator causes the Lewis acid to precipitate by interacting with the amine. More sterically hindered amines can prevent this interaction with the Lewis acid. Addition of stronger Lewis bases that effectively compete with the accelerator for the Lewis acid is also possible. Room temperature polymerization can also be initiated without accelerators by using a strong visible light source. For example, the salt-polymer powder complex to which an initiator is added can be mixed with a liquid phase comprised of the monomer (e.g., methyl methacrylate) and a cross-linking agent, e.g. TEG, and the mixture exposed to the light source.

As an alternative to dissolving the heavy metal salt in monomer(s) followed by polymerization, the homogeneous heavy metal salt-polymer complexes may be formed by film casting methods and solvent evaporation. Incorporation of bismuth tribromide, for instance, in poly(methyl methacrylate) to form films for transparent radiopaque shields can be performed by dissolving the polymer and salt in a common solvent like THF. Thus, a 12.5 percent by weight solution of bismuth tribromide in THF containing the dissolved poly(- methyl methacrylate) can be cast as a film and the solvent allowed to slowly evaporate.

Radiopaque polyesters of the present invention may be prepared by dissolving the heavy metal salt in a polyol, e.g. ethylene glycol. The dissolved salt is then mixed with a dicarboxylic acid, e.g. terephthalic acid, phthalic anhydride, and polymerized at elevated temperatures in the presence of an antimony catalyst.

As previously mentioned, the radiopaque heavy metal salt-polymer complexes have a wide variety of dental and medical applications, including industrial uses. In the dental and medical fields, the radiopaque polymers may be employed in applications normally calling for acrylic polymers and vinyl-acrylic copolymers. This would include resin systems having low levels of crosslinking which for purposes of the present invention range from 0 to about 5 percent, and denser more rigid structures having a higher degree of crosslinking ranging from more than 5 to about 15 percent. Such systems include "self-curing" type resins which react at ambient temperatures of between 25° and 30° C., and systems which cure at elevated temperatures of about 65° to 100° C. with the application of heat.

Generally, for preparing radiopaque biomedical resins, i.e. polymer compositions having useful applications in restorative dentistry and medicine, the heavy metal-polymer complex would be ground to a fine powder and used as a component of a two-part system. More specifically, in the two-part system the composition is furnished in two separate containers. The first container would comprise a powder containing a mixture of the radiopaque polymer complex previously described, fillers and initiator-like benzoyl peroxide or ABIN. The second container comprises a liquid containing methyl methacrylate monomer or BisGMA and a crosslinking agent like ethylene glycol dimethacrylate. When the solutions are mixed and exposed to a strong visible light, the radiopaque polymer complex will swell in the methyl methacrylate monomer and polymerize into a solid homogeneous polymeric mass.

Applications for the radiopaque polymer complexes having low levels of crosslinking include removable dental devices like dentures, partial dentures, bite splints, night guards, orthodontic space maintainers, maxillofacial devices and other nonfixed devices where there is a risk of accidental impaction into the respiratory or digestive tracks. These radiopaque polymer complexes, having low levels of crosslinking, can also be formulated into bone cements for bonding implanted devices to bone tissues so as to permit monitoring by noninvasive methods.

The second category of biomedical resins include highly crosslinked structures where radiopacity is also a desirable property. They include fixed structures like restorative resins, veneering facings for dental crowns and bridges, dental and surgical implants, root canal sealants and other dental, surgical and implant applications. These materials are generally provided to the user as a two-part system which upon mixing cures at ambient temperatures either by combining the initiator and the accelerator, or by decomposing the initiator with a light source. In the highly crosslinked structures, however, no preformed polymer is used. Instead, each component consists of a solution of monomers. Many of such applications can also employ a hard, inert reinforcing "filler" consisting of a finely divided material such as silica.

In addition to the foregoing medical/dental applications, the radiopaque polymer complexes may be used with all body implants, prosthetic devices and appliances which are presently used with radiolucent plastics, such as catheters, bone implants, heart valves, arteries, etc.

Industrial applications for the radiopaque complexes of the present invention include x-ray and other radiation shielding devices. Optionally, the transparent radiopaque polymers, which are also opaque to U/V radiation, can be used in such areas as aircraft windows and cabins for shielding pilots and astronauts from high energy U/V and x-radiation found at high altitudes. Transparent shielding devices made of sheets of radiopaque poly(methyl methacrylate) for workers exposed to x-rays and other forms of potentially harmful radiation are also intended utilities. The radiopaque polyester complexes are especially useful in textiles and fabrics for making specialized radiopaque garments to be worn by workers exposed to radiation in the job place.

The following specific examples demonstrate the radiopaque polymers, resin compositions and products made therefrom according to the present invention. However, it is to be understood that these examples are for illustrative purposes only and do not purport to be wholly definitive as to conditions and scope.

EXAMPLE I

PART A

Fifteen samples of a heavy metal salt-radiopaque polymer complex were prepared with varying concentrations of bismuth tribromide dissolved in methyl methacrylate monomer. The bismuth tribromide was used in the anhydrous form with 0.5 percent by weight ABIN initiator based on monomer. The amount of bismuth tribromide ranged from 0.0044 percent to 40 weight percent, or a methyl methacrylate:bismuth tribromide ratio of 10,000:1 to 6.7:1. Each sample was placed in a test tube with a serum cap; flushed with nitrogen; sealed and bulk polymerized for 48 hours at 65° C. Those polymer samples with percentages of bismuth tribromide of 20 weight percent or less were found to be transparent and colorless. Polymers having over 20 weight percent bismuth tribromide developed a yellowish hue. However, all samples were found to be hard, homogeneous and transparent.

PART B

The radiopaque polymers of Part A were tested to develop data on the presence of uncomplexed bismuth tribromide by differential scanning calorimetry using a Perkin Elmer DSC-4 instrument. Scans were run from 60° to 330° C. with a scan rate of 20° C. per minute.

TABLE I

| Weight % BiBr$_3$ | Tg °C. |
|---|---|
| 0 | 108. |
| 0.0044 | 109. |
| 0.044 | 114. |
| 0.44 | 117. |
| 1.0 | 119. |
| 4.25 | 121. |
| 35 | 123. |
| 100 | none |

The data in Table I show a gradual increase in the glass transition temperature on increasing the salt content, but in none of the samples is the 269° melt peak of BiBr$_3$ evident. Also, the fact that the polymers having up to 40 percent by weight bismuth tribromide were found to be transparent supports the conclusion that all samples were fully complexed and that no free bismuth tribromide was present.

PART C

Bismuth tribromide-poly(methyl methacrylate) complexes containing 5; 9; 10; 11; 13; 15; 20; 25; 30; 35; and 40 weight percent bismuth tribromide were pressed into 1 mm pellets and placed on a Kodak x-ray film along with an aluminum stepwedge with 1 mm steps. The film was placed 22 inches below the cathode ray tube of an x-ray apparatus and exposed to 90 Kv 6 MAS x-rays. Using a microfilm densitometer the x-ray absorption of the pellets was then compared with that of the aluminum stepwedge. It was found that 12.5 percent by weight bismuth tribromide was required in a 1 mm pellet to provide the same radiopacity as a 1 mm pellet of aluminum.

EXAMPLE II

PART A

Poly (methyl methacrylate)-bismuth tribromide radiopaque complexes were prepared with a crosslinking agent. To prevent possible leaching of the bismuth tribromide the complex was encapsulated in an interpenetrating network. For each sample, the bismuth tribromide was first dissolved in methyl methacrylate monomer at room temperature. 0.5 percent ABIN initiator and tetraethylene glycol dimethacrylate crosslinking agent were added to the solutions at 1; 4; 6 and 15 percent by weight. The solutions were bulk polymerized at 65° C. for 48 hours to insure maximum polymerization. The polymer samples were ground into a powder for incorporation into a matrix of poly(methyl methacrylate). This was performed by swelling the polymer complex in methyl methacrylate monomer. Instead of using benzoyl peroxide with the accelerator dimethyl-p-toluidine, the swelled samples were polymerized with ABIN under nitrogen. Those samples having 6 and 15 percent crosslinking agent did not swell in the monomer and produced poor encapsulations. In order to produce a final product having 12.5 percent by weight bismuth tribromide, less than 4 percent crosslinked complexes with 30, 35 and 40 percent bismuth tribromide were diluted down to 12.5 percent by weight bismuth tribromide with methyl methacrylate monomer and polymerized to provide good homogeneous encapsulations.

PART B

Studies were performed to determine the leachability of bismuth tribromide from encapsulated and nonencapsulated samples. In the case of complexed, noncrosslinked bismuth tribromidemethyl methacrylate films complexes were prepared for greatest surface area according to the following procedure: 12.5 percent by weight bismuth tribromide and 0.5 percent by weight ABIN were dissolved in methyl methacrylate and mixed. This was injected between two glass plates separated by a Teflon ring and wrapped with Teflon tape to hinder evaporation. The plates were placed in a vacuum oven at 65° C. for 48 hours and polymerized. Clear homogeneous films resulted. The films were weighed and placed in water for 14 days. Subsequently, the films were removed, dried and reweighed with no loss of weight. The water the film was in was tested for bromine with silver nitrate. No trace of bromine was found. The water was also tested for bismuth with concentrated hydrochloric acid (BiOCl forming as a white precipitate if bismuth is present) with no trace of bismuth found. Moreover, the film itself was clear indicating that no bismuth hydroxide formed. Bi (OH$_3$) would have made the film cloudy. Hence, even without encapsulation, no leaching of bismuth tribromide was observed.

The same tests were performed on the encapsulated samples with the same results, namely, no leaching of bismuth or bromine occurred, and there was no weight loss, cloudiness or loss of radiopacity.

EXAMPLE III

A sheet of film comprising bismuth tribromide-poly(methyl methacrylate) complex was prepared by solvent evaporation from ethyl acetate. Poly(methyl methacrylate) and bismuth tribromide, 12.5 percent by weight based on the poly(methyl methacrylate), were dissolved in the ethyl acetate and mixed for several hours. The solution was cast as a film and the ethyl acetate allowed to evaporate slowly under nitrogen for 48 hours to provide a transparent film.

EXAMPLE IV

Following the method of Example III a solvent evaporation radiopaque complex was prepared with polyvinyl acetate and 12.5 percent by weight bismuth tribromide. The salt and polymer were dissolved in a 20 percent solution of ethyl acetate and mixed thoroughly. A film was then cast and the solvent slowly evaporated off. The resulting membrane was clear, homogeneous and radiopaque.

EXAMPLE V

PART A

Bismuth trichloride was also combined with methyl methacrylate to form radiopaque complexes. These complexes were prepared following the same methodology of Example I. However, bismuth trichloride was less soluble than bismuth tribromide in methyl methacrylate. Consequently, complexes with a BiCl$_3$ content above 7.0% were cloudy, nonhomogeneous and far less transparent than those prepared with bismuth tribromide. Several ratios of the above complexes were prepared: $1 \times 10^{-4}$, $10^{-3}$ and $10^{-2}$ molar BiCl$_3$; 3.5%, 7.0%, 10.010.5%, 14.0% and 20% by weight BiCl$_3$.

PART B

Four pellets were made from the bismuth trichloride complexes. These 1 mm pellets were placed on x-ray film 22 inches below the x-ray tube and exposed to 90 Kv 6 MAS x-rays. The resulting film was run on the film microdensitometer to determine their exact radiopacities. From the data developed it was found that it would require 15 percent by weight bismuth trichloride in a 1 mm pellet to equal the radiopacity of 1 mm aluminum.

EXAMPLE VI

A polyester radiopaque complex was prepared by heating in a round-bottom flask 1.23 g glycerol, 2.96 g phthalic anhydride and 0.47 g bismuth trichloride. The temperature was slowly raised to 200° C. with stirring. The temperature was held at 200° C. for 2 hours. The resulting polyester had a bismuth tribromide content of 10 percent by weight and had a tan hue.

EXAMPLE VII

Radiopaque polyester complexes of the type prepared in Example VI are also prepared by either batch or continuous-polymerization, or by direct spinning methods. The batch method employs a catalyzed ester exchange reaction between molten dimethyl terephthalic and glycol-containing dissolved bismuth tribromide to provide a mixture of monomer, low molecular weight polymer and methanol which can be distilled off at about 150° C. The monomer is then polymerized in the presence of an antimony catalyst. Additives like $TiO_2$ can be added and with controlled agitation and reduction in pressure, excess glycol removed at a temperature of about 280° C. Heating is continued until the desired degree of condensation is obtained.

Spinning the radiopaque polyester can be performed by known methods, e.g. formation of filaments by forcing molten polymer at about 285° C. through a sand-bed filter to a spinneret containing many holes of 0.009 inches in diameter. Extruded filaments are quenched by means of a forced air system resulting in solidification. Several threadlines are brought together, coiled and wound for further drawing. In order to produce the desired oriented crystalline structure for the desired strength, modulus, recovery, abrasion resistant properties, etc., the amorphous spun filaments can be drawn to about four times their length.

The radiopaque polyester fibers can also be blended with cotton or wool, e.g. 50/50 blend. The polyesters are also dyable. The radiopaque polyester filament yarns are especially desirable for knitting fabrics, i.e. double jersey fabrics for protective garments for shielding from potentially harmful radiation exposure.

EXAMPLE VIII

A biomedical resin for molding a dental implant composition is prepared from a heavy metal radiopaque polymer complex by first dissolving 40 percent by weight bismuth tribromide in methyl methacrylate monomer and polymerizing the solution with ABIN at 65° C. A solid polymeric material forms which is ground to a fine powder. 0.5 percent by weight benzoyl peroxide initiator is deposited in the powder to form the solid phase.

Separately, the liquid monomer phase is prepared by combining methyl methacrylate monomer with TEG crosslinking agent. The liquid and solid phases are combined producing a swelling of the polymer into a dough-like material due to polymerization of the composition. The dough is placed in a gypsum mold where it is allowed to cure at 65° C.

EXAMPLE IX

A translucent radiopaque device for shielding x-rays can be prepared with a bismuth bromide-poly(methyl methacrylate) complex containing 12.5 percent bismuth tribromide based on weight of poly(methyl methacrylate). A film of the polymer complex is formed by casting from THF containing the dissolved polymer and salt. The solvent is very slowly removed under a stream of nitrogen to produce a clear, transparent film. To form a shielding film with a radiopacity equivalent to 1 mm of aluminum the film should also be 1 mm in thickness.

EXAMPLE X

A flexible catheter prepared with a molding composition comprising a copolymer in which one of the monomer units contains a carbonyl group for complexation to a heavy metal salt, for example, a polysiloxane-acrylate copolymer. The heavy metal salt would be incorporated in sufficient quantity to impart a radiopacity comparable with aluminum. Salt incorporation may be achieved by solvent evaporation of a copolymer-salt solution or prior to polymerization of the Lewis base monomer. The molding will result in tough, flexible, nontoxic and radiopaque catheter devices.

While the invention has been described in conjunction with examples thereof, this is illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

What is claimed is:

1. A medical device fabricated at least in part from a composition comprising a radiopaque polymer, said polymer derived from a heavy metal Lewis acid radiopacifying salt and at least one Lewis base monomer selected from the group consisting of alkyl and vinyl alkyl ketones, alkyl and aryl esters of unsaturated carboxylic acids, vinyl esters of carboxylic acids, cellulose esters of carboxylic acids, linear and crosslinked polyesters, said salt being molecularly bound to said polymer to form a clear, homogeneous, substantially nonleachable material, said composition being substantially free of unbound radiopacifying salt.

2. The medical device of claim 1 which is a prosthetic device.

3. The medical device of claim 1 which is a medical appliance.

4. The medical appliance of claim 3 which is a catheter.

5. The prosthetic device of claim 2 selected from the group consisting of bone implant, heart valve and blood vessel.

6. The medical device of claim 1 wherein the radiopacifying salt of the composition is a compound comprising a cation selected from heavy metals having atomic numbers of 57 to 92 and an anion capable of solubilizing the salt into the polymer.

7. The medical device of claim 6 wherein the cation of the salt is bismuth.

8. A medical device fabricated at least in part from a composition comprising a radiopaque polymer, said polymer derived from a Lewis acid radiopacifying salt comprising a heavy metal having an atomic number from 57 to 92 and at least one Lewis base monomer selected from the group consisting of alkyl esters of unsaturated mono and dicarboxylic acids, vinyl esters of aliphatic and aromatic monocarboxylic acids and esters of the formula:

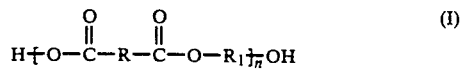

wherein R is aryl or $(CH_2)_y$ wherein y is an integer of 1 to 10, $R_1$ is aryl, substituted aryl or $(CH_2)_x$ wherein x is an integer of 1 to 6 and n is an integer of 2 to 5000, said radiopacifying salt being present in an amount sufficient to impart a radiopacity to the polymer which is at least equivalent to that of aluminum and which will also dissolve in the monomer, said salt being molecularly bound to said polymer to form a clear, homogeneous, substantially nonleachable material, said composition being essentially free of unbound radiopacifying salt.

9. A dental device fabricated at least in part from a composition comprising a radiopaque polymer, said polymer derived from a heavy metal Lewis acid radiopacifying salt and at least one Lewis base monomer selected from the group consisting of alkyl and vinyl alkyl ketones, alkyl and aryl esters of unsaturated carboxylic acids, vinyl esters of carboxylic acids, cellulose esters of carboxylic acids, linear and crosslinked polyesters, said salt being molecularly bound to said polymer to form a clear, homogeneous, substantially nonleachable material, said composition being substantially free of unbound radiopacifying salt.

10. The dental device of claim 9 which is a member selected from the group consisting of denture, crown, bridge, prosthesis, implant, splint, guard, space maintainer and maxillofacial device.

11. The dental device of claim 9 wherein the radiopacifying salt of the composition is a compound comprising a cation selected from heavy metals having atomic numbers of 57 to 92 and an anion capable of solubilizing the salt into the polymer.

12. The dental device of claim 11 wherein the cation of the salt is bismuth.

13. A dental device fabricated at least in part from a composition comprising a radiopaque polymer, said polymer derived from a Lewis acid radiopacifying salt comprising a heavy metal having an atomic number from 57 to 92 and at least one Lewis base monomer selected from the group consisting of alkyl esters of unsaturated mono and dicarboxylic acids, vinyl esters of aliphatic and aromatic monocarboxylic acids and esters of the formula:

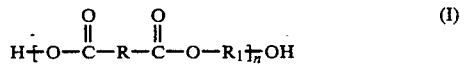

(I)

wherein R is aryl or $(CH_2)_y$ wherein y is an integer of 1 to 10, $R_1$ is aryl, substituted aryl or $(CH_2)_x$ wherein x is an integer of 1 to 6 and n is an integer of 2 to 5000, said radiopacifying salt being present in an amount sufficient to impart a radiopacity to the polymer which is at least equivalent to that of aluminum and which will also dissolve in the monomer, said salt being molecularly bound to said polymer to form a clear, homogeneous, substantially nonleachable material, said composition being essentially free of unbound radiopacifying salt.

14. A radiation shielding device comprising at least in part a composition comprising a radiopaque polymer, said polymer derived from a heavy metal Lewis acid radiopacifying salt and at least one Lewis base monomer selected from the group consisting of alkyl and vinyl alkyl ketones, alkyl and aryl esters of unsaturated carboxylic acids, vinyl esters of carboxylic acids, cellulose esters of carboxylic acids, linear and crosslinked polyesters, said salt being molecularly bound to said polymer to form a clear, homogeneous, substantially nonleachable material, said composition being substantially free of unbound radiopacifying salt.

15. A radiation shielding device comprising at least in part a composition comprising a radiopaque polymer, said polymer derived from a Lewis acid radiopacifying salt comprising a heavy metal having an atomic number from 57 to 92 and at least one Lewis base monomer selected from the group consisting of alkyl esters of unsaturated mono and dicarboxylic acids, vinyl esters of aliphatic and aromatic monocarboxylic acids and esters of the formula:

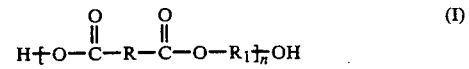

(I)

wherein R is aryl or $(CH_2)_y$ wherein y is an integer of 1 to 10, $R_1$ is aryl, substituted aryl or $(CH_2)_x$ wherein x is an integer of 1 to 6 and n is an integer of 2 to 5000, said radiopacifying salt being present in an amount sufficient to impart a radiopacity to the polymer which is at least equivalent to that of aluminum and which will also dissolve in the monomer, said salt being molecularly bound to said polymer to form a clear, homogeneous, substantially nonleachable material, said composition being essentially free of unbound radiopacifying salt.

16. A fabric comprising a radiopaque polyester, said polyester being derived from a Lewis acid radiopacifying salt comprising a heavy metal having an atomic number from 78 to 92 and at least one Lewis base monomer selected from the group consisting of alkyl esters of unsaturated mono and dicarboxylic acids, vinyl esters of aliphatic and aromatic monocarboxylic acids and esters of the formula:

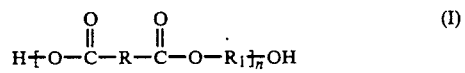

(I)

wherein R is $C_6H_4$, $R_1$ is $(CH_2)_x$ wherein x is 1 and n is between 2 to 5000, said radiopacifying salt being present in an amount sufficient to impart a radiopacity to the polymer which is at least equivalent to that of aluminum and which will also dissolve in the monomer, said salt being molecularly bound to said polymer to form a clear, homogeneous, substantially nonleachable material, said polyester being essentially free of unbound radiopacifying salt.

17. The radiopaque polyester fabric of claim 16 wherein the polyester is polyethylene terephthalate.

18. A garment made with the radiopaque polyester fabric of claim 16.

19. A garment made with the radiopaque polyester fabric of claim 17.

20. A two phase radiopaque composition comprising a solid phase and a liquid phase, said solid phase comprising a radiopaque polymer derived from a heavy metal Lewis acid radiopacifying salt and at least one Lewis base monomer selected from the group consisting of alkyl and vinyl alkyl ketones, alkyl and aryl esters of unsaturated carboxylic acids, vinyl esters of carboxylic acids, cellulose esters of carboxylic acids, linear and crosslinked polyesters, said salt being molecularly bound to said polymer to form a clear, homogeneous, substantially nonleachable material, said liquid phase comprising a monomer solution, said composition formed by swelling the solid phase in the liquid phase and polymerizing into a solid homogeneous mass substantially free of unbound radiopacifying salt.

21. A multiple container package for preparing the two phase radiopaque polymer composition of claim 20 comprising first and second containers, said first container comprising said radiopaque polymer composition and an initiator, said second container comprising a monomer solution and a crosslinking agent.

22. The multiple container package of claim 21 wherein the monomer of the second container is selected from the group consisting of esters of acrylic acid, methacrylic acid, and ethacrylic acid.

* * * * *